United States Patent [19]
Michels

[11] Patent Number: 5,533,517
[45] Date of Patent: Jul. 9, 1996

[54] CYTOLOGICAL SAMPLING METHOD AND DEVICE

[75] Inventor: Ruth Michels, Grand Junction, Colo.

[73] Assignee: St. Mary's Hospital and Medical Center, Inc., Grand Junction, Colo.

[21] Appl. No.: 322,103

[22] Filed: Oct. 12, 1994

Related U.S. Application Data

[62] Division of Ser. No. 52,407, Apr. 23, 1993, Pat. No. 5,357,977.

[51] Int. Cl.$^6$ .................................................. A61B 10/00
[52] U.S. Cl. ........................................ 128/758; 604/314
[58] Field of Search ............................. 128/749, 752, 128/758, 759, 760, 771; 604/317–319, 403, 404

[56] References Cited

U.S. PATENT DOCUMENTS

| | | | |
|---|---|---|---|
| 3,540,432 | 11/1970 | Ayra | 128/2 |
| 3,661,144 | 5/1972 | Jensen et al. | 128/758 |
| 3,863,624 | 2/1975 | Gram | 128/758 |
| 3,889,657 | 6/1975 | Baumgarten | 128/758 |
| 4,250,892 | 2/1981 | Dolhey et al. | 128/758 |
| 4,257,425 | 3/1981 | Ryan | 128/758 |
| 4,393,879 | 7/1983 | Milgrom | 128/758 |
| 4,620,548 | 11/1986 | Hasselbrack | 128/758 |
| 4,627,444 | 12/1986 | Brooker | 128/758 |
| 4,628,940 | 12/1986 | Näslund | 128/750 |
| 4,633,886 | 1/1987 | Bucaro, Jr. | 128/749 |

OTHER PUBLICATIONS

"Data on Automated Cytology Systems as Submitted by Their Developers", pp. 300–306, 1991, Analytical and Quantitative Cytology and Histology, vol. 13, No. 4, Aug.

"Letters to the Editor", p. 578, 1987, The Journal of Family Practice, vol. 24, No. 6.

Baker, "Improving the Adequacy of Pap Smears", pp. 109–114, 1989, AFP, vol. 39, No. 6, Jun.

Bibbo, "What You Should Know About Papanicolaou Smears", pp. 104–107, Diagnostic Cytopathology, vol. 5, No. 1 1989.

Blenkinsopp et al., "Cervical Smears: Choice of Spatula is Critical", p. 986, 1986, The Lancet, Oct. 25.

Lundberg, "Quality Assurance in Cervical Cytology", pp. 1672–1679, 1989, JAMA, vol. 262, No. 12, Sep.

Mauney et al., "Rates of Condyloma and Dysplasia in Papanicolaou Smears With and Without Endocervical Cells", pp. 18–21, 1990, Diagnostic Cytopathology, vol. 6, No. 1.

Osha Bloodborne Pathogens Standard, pp. 64175–64182, Rules and Regulations §1910.1030, Federal Register, vol. 56, No. 235, Dec. 6, 1991.

Primary Examiner—Max Hindenburg
Attorney, Agent, or Firm—Sheridan Ross & McIntosh

[57] ABSTRACT

A method and device for collecting cytological samples is provided for suctioning material into a fixative container containing a sufficient amount of fixative so that collected cytological material is fixed substantially immediately after dislodgement. The sampling device includes a means for dislodging cytological material from the cervix uteri, a means for suctioning uterine cervical tissue under negative pressure, and a means for fixing collected cytological material. The sampling method and device is particularly useful for collecting cytological samples for morphological analysis and for collecting potentially HIV-infected cytological material without significant exposure to the healthcare worker.

16 Claims, 2 Drawing Sheets

CYTOLOGICAL SAMPLING METHOD AND DEVICE

This is a divisional application of application Ser. No. 08/052,407, filed Apr. 23, 1993, U.S. Pat. No. 5,357,977.

FIELD OF THE INVENTION

The present invention relates to a method and device for sampling cytologic material, and particularly to a method and device for preparing papanicolaou smears.

BACKGROUND OF THE INVENTION

Diagnostic cytology has been used extensively as a detection system for alterations in cellular morphology, such as alterations which may occur when a normal cell develops into a cancerous cell. One of the main applications of diagnostic cytology is in the early detection of cervical cancer. For over three decades, the Papanicolaou (PAP) smear has been used as a routine screening procedure for neoplastic and pre-neoplastic cells isolated from the cervix uteri. Neoplastic cells generally refer to benign transformed cells (tumor cells) and malignant transformed cells (cancerous). Recently, however, national controversy has surrounded the accuracy of PAP smear testing. Statistics indicate that as high as 50% of all PAP smears performed may result in false negatives due to sampling error. This statistic reflects that while many women may be diagnosed as normal at the time of testing, they may actually have pre-malignant or malignant cells that are incorrectly sampled or incorrectly evaluated. Thus, a statistically significant number of mortalities occur from cervical cancer due to inadequate testing techniques.

The principal aspects affecting the accuracy of PAP smears are the reliability of the cell sampling techniques used and the skill of cytotechnologists to accurately evaluate and report the cell sample analysis. Accurate and meaningful results can only be obtained if the cell sampling technique is efficient with respect to the collection, fixation and staining of desired cells. Thus, the potential for error in the sampling and evaluation stages of conventional procedures has prompted the need for improved standardization of PAP smear collection methods and devices.

Prior attempts have been made to standardize the interpretation of collected cells. Several automated cytological specimen screening devices are commercially available that will allow healthcare workers to pre-screen the cytological specimens, thus providing some degree of standardization with respect to the parameters used to classify cells as normal or abnormal. Because such automated devices address solely h problem of unreliable cell sample analysis, there remains a need to address the significant problems encountered in the collection and preparation of cell samples.

Cell samples are typically removed from the mucous membrane of the cervix uteri by scraping the tissue with a spatula or a cotton swab. Once collected, the cell sample is smeared onto a glass plate or slide, sprayed with a conventional fixative, stained, mounted with a coverslip, and examined under a microscope. A major problem in performing PAP smears in this manner is that any cells that are exposed to air before being fixed assume morphologies that are distorted and difficult to evaluate. One of the predominant characteristics of an abnormal cell is its relationship of the nucleus to the cytoplasm and the ability of evaluating the DNA content of that nucleus. Morphological changes to pre-cancerous or cancerous cells can be artifactually masked by artifactual distortion caused by exposure of the cells to air, such distortion making cancerous cells appear to be normal resulting in false negative PAP smear tests. The problem caused by morphological changes resulting from exposure of collected cells to air is exacerbated when, as is often done, multiple samples are obtained from different anatomic sites of a patient prior to the fixation of an individual cell sample obtained from any one particular sample site.

In addition to inaccurate PAP smear results caused by exposure of cell samples to air, false negative tests often result from sampling an inadequate number of particular endocervical cells. It is known that there is a "transformation zone" where columnar cells transform into squamous cells. If a sufficient number of cells are not sampled from this "zone", then neoplastic cells may go undetected.

Prior investigators have taught the use of various devices for the collection of cells from cervical uteri. These devices, however, do not adequately address the sampling problems described above. For example, U.S. Pat. No. 3,540,432 by Ayre, issued Nov. 17, 1970, describes an instrument for sampling cervical tissue. The instrument comprises, a pipet containing glycerol and a bulb attached to one end of the pipet. In a two-stage process, cells are collected by squeezing the pipet bulb and releasing it while scraping the head of the pipet along the tissue. Ayre discloses that some cells are drawn into the pipet while others remain outside on the pipet head. Cells are then transferred from the instrument into glycerol contained in a cap by squeezing the attached pipet bulb thereby expelling the cells by air. Cells can be collected in the instrument at home and then mailed to a laboratory for cytological analysis. U.S. Pat. No. 4,620,548 by Hasselbrack, issued Nov. 4, 1986, describes an elongated spatula for scraping and collecting cells. The spatula is attached to a bulb or syringe. Cells are collected into the aspiration tube by squeezing the attached bulb. The attached bulb is again squeezed to eject the cells by air onto a microscope slide. The leading edge of the spatula is then rubbed in the pool of ejected cells to remove cells remaining on the outside of the spatula. The cells are then spread across the face of a glass slide, and finally fixed using a conventional spray-type fixative. U.S. Pat. No. 4,633,886 by Bucaro, issued Jan. 6, 1987, describes a two-stage process using a device consisting of an elongated tube having a plunger and a separate chamber containing a fixative solution. Cells are drawn into the tube containing a preservative using the plunger and the tube is then interlocked with the separate fixative-containing chamber. The fixative is permitted to flow and mix with the collected cells.

Another major problem in performing PAP smears is the safe management of the cell sample when collecting cells from individuals potentially infected with HIV. With the onset of the AIDs epidemic, it has become critical that healthcare workers minimize their contact with human tissue and/or body fluids. The Occupational Safety and Health Administration (OSHA) has set forth extensive guidelines for protecting healthcare workers against the hazards of exposure to potentially infected human tissue and/or bodily fluids. Under OSHA regulations, human bodily fluids include semen, vaginal fluids, cerebrospinal fluid, synovial fluid, pleural fluid, pericardial fluid, peritoneal fluid, amniotic fluid, saliva, and any body fluid that is visibly contaminated with blood, and all body fluids where it is difficult or impossible to differentiate between body fluids. OSHA guidelines specifically indicate that all procedures involving blood or other potentially infectious materials shall be performed in such a manner as to minimize splashing, spraying, spattering, and generation of droplets of these substances and that specimens of blood or other potentially infectious materials shall be placed in a container which prevents leakage during collection, handling, processing, storage, transport, or shipping (29 U.S.C. 653 §1910.1030 (1991)). Conventional methods for collecting PAP smears requires direct contact with the tissue sample by post-collection manipulation of the tissue sample, thereby increasing the risk of contact with the tissue sample and/or body fluids.

To overcome the problem of healthcare worker direct contact with human tissue and/or body fluids, as well as the problem of inaccurate testing due to morphological changes of cell samples prior to fixation, it would be desirable to have a method and device that would allow sampling of cells in a system that prevents exposure of collected cells to air and alleviates significant exposure of healthcare workers to collected cells. Such a method and device would eliminate sampling errors and standardize means of evaluating cell samples, decreasing the number of false negatives, preventing undue exposure of healthcare workers to potentially infectious agents, and resulting in the saving of human lives.

SUMMARY

The present invention relates to a novel method and device for sampling cytologic material. The method and device are particularly useful for preparing samples for morphological analysis such as papanicolaou smears. In one embodiment of the present invention, cytological material is dislodged from a cervix uteri using a sampling instrument. Negative pressure is continually applied to the sampling instrument during the process to allow collection of a predetermined amount of cytological material. The continuous negative pressure applied to the collection device of the present invention dislodges the cellular sample and immediately deposits it directly into a sealed vessel containing a sufficient amount of fixative to immediately fix the cytological material. Cytological material is contacted with fixative within from about 0.5 seconds to about 5 seconds following collection of the material from the cervix uteri. Thus, the cytological material does not undergo significant morphological change due to exposure to air outside of the sealed fixative container.

In one embodiment, the device of present invention comprises a means for dislodging cytological material from uterine cervical tissue, a means for suctioning cytological material under negative pressure, and a means for fixing collected cytological material. The dislodging means is designed to disengage cells from the cervix uteri. The suctioning means is a source of negative pressure that can be regulated such that a pre-determined amount of cytological material may be collected. The fixing means is designed to store a sufficient amount of fixative to fix cells substantially immediately in a sealed environment.

DETAILED DESCRIPTION OF THE INVENTION

Figure 1:
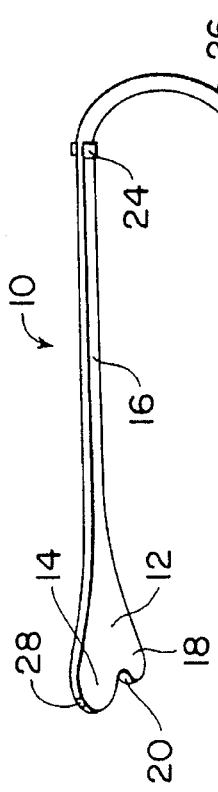
FIG. 1 is a schematic diagram of one embodiment of the cytological sampling device of the present invention.

The method and device of the present invention is useful for sampling cytological material from animals. As used herein, sampling cytological material refers to removing individual cells or layers of cells from the tissue of a desired subject for examination purposes. Cytological examination of cells may be performed for several reasons, including but not limited to, the detection of morphological changes and the identification and determination of the physical location of cellular products and components. Cytological material may be sampled to detect morphological changes in cells undergoing, for example, malignant cell metamorphosis and cellular atrophy. It is important in cytological examinations To maintain the morphology of the cytological samples as close to the morphology of cells in vivo so that small differences between normal and abnormal cells can be accurately detected.

The present invention is also useful for identifying and determining the physical location of cell products inside or attached to particular cells. Analysis of certain diseases requires collection of cytological material in a manner such that the location of specific cellular components can be determined by reference to a cell's in vivo morphology. Such products and components can include enzymes, proteins, carbohydrates, and infectious agents such as viruses, bacteria and parasites.

The method and device of the present invention is particularly useful for sampling mucous membrane cells to detect abnormal cell morphology. Mucous membrane cells are conducive to analysis due to their location in accessible sites such as the uterine cavity and the oral cavity. Mucous membranes include epithelium, lamina propria, and in the digestive tract, smooth muscle. Epithelium cell types include squamous, simple cuboidal, ciliated columnar, pseudostratified ciliated columnar, stratified squamous and transitional cells. Mucous membranes are often sites where neoplastic cells can occur. Detection of neoplastic mucous membrane cells is typically performed by isolating cells and examining the morphology of the cells under a microscope. Predominant characteristics of neoplastic epithelium cells include the morphological transformation of single cells, as well as the peculiar ranization of groups of neoplastic cells. The morphology of neoplastic cells is typified by a partial or complete lack of the normal structural organization or functional coordination which forms normal tissue. Groups of neoplastic cells often form masses of tissue and the shape and size of individual cells change as the cells become more neoplastic.

In one embodiment of the present invention, cells from the cervix uteri are sampled to detect possible morphological changes in cell structure indicating pre-cancerous and cancerous conditions. The cervix uteri connects the vagina and the uterine cavity. There is a line of columnar epithelium of the endocervix which forms a substantially sharp line where the cells meet the squamous epithelium that covers the portion of the cervix protruding into the vagina. This relatively sharp line is referred to as the squamocolumnar junction of the cervix. Cytological material that can be collected for purposes of analysis include cells from the ectocervix, the squamocolumnar junction, and the endocervical canal of the cervix uteri. A major lesion of the cervix is carcinoma of the squamous cells of the vaginal portion of the cervix. Morphologically, neoplastic squamous epithelium can vary in shape, size, polarity, pattern, and staining reactions. Other forms of cervical cancer include adenocarcinomas, which typically have a glandular-type structure but also can vary in size, shape, and staining pattern. The differences between normal and transformed cells, as well as the differences between different types of transformed cells, can be small and difficult to detect. Therefore, the morphology of sampled cells must be carefully maintained to allow detection of such differences in sampled cells.

The method and device of the present invention is designed to prevent substantial morphological changes from occurring during the collection and transporting of cytological material. As used herein, substantial morphological changes refers to any changes in the morphology of cells that would compromise the accuracy of the morphological analysis of those cells. The method and device of the present invention is capable of substantially maintaining the in vivo morphology of collected cells. Moreover, the method and device of the present invention enables the healthcare worker to collect a relatively uniform number of cells in each sample and to fix the sample in such a manner so as to maintain its morphological structure without substantial exposure of the healthcare worker to the collected human tissue and/or body fluid sample.

In one embodiment, the device of the present invention comprises a means for dislodging cytological material 10, a means for suctioning cytological material under negative pressure 30, and a means for fixing cytological material 32. The dislodging means 10 comprises any instrument suitably designed for contacting mucous membrane tissue and for effectively dislodging desired cells. The dislodging means preferably comprises a sampling instrument 10 which enables the healthcare worker to directly contact the instrument 10 to the tissue to be sampled such as by passing the instrument 10 along the tissue in a scraping motion to disengage cells.

In one embodiment, referring to FIG. 1–4, cytological material is dislodged by a sampling instrument 10 comprising an elongated instrument having a handle with distal 12 and proximal ends 24 extending lengthwise from the handle 16. The distal end 12 of the sampling instrument 10 is the portion of the sampling instrument 10 which contacts the tissue being sampled. As such, the distal end 12 is preferably shaped to enable the healthcare worker to collect an effective number of cells in a minimum amount of time. The distal end 12 may be essentially flat, rounded, beveled, conical, or tubular shaped. The distal end 12 preferably comprises two opposite planar surfaces extending from the handle 16 of the sampling instrument 10, each planar surface being sufficiently flat to form a spatula shape. Preferably, each planar surface is rounded to facilitate dislodgement of cells without damaging the morphology of the cells or substantially injuring the tissue.

In a preferred embodiment, the distal end 12 of the sampling instrument 10 is suitably designed for dislodging cytological material from the squamocolumnar junction of the cervix uteri. The planar surfaces of the distal end 12 of the sampling instrument 10 comprise a frontal lobe 14 and a lateral lobe 18 projecting from the handle 16. Each planar surface of the distal end 12 also comprises a u-shaped transition section 20 directly connecting the frontal 14 and lateral 18 lobes. The transition section 20 enables the planar surfaces of the distal end 12 to pass smoothly over curved surfaces of tissue. The leading edge of the distal end 12 of the sampling instrument 10 has a blunt shape, being flat or rounded to enable the distal end 12 to pass smoothly over the surface of tissue being sampled. The sampling instrument 10 also comprises a tubular channel passing lengthwise through the sampling instrument. The diameter of the tubular channel is sufficient to provide passage of collected cells through the length of the sampling instrument 10.

The proximal end 24 of the sampling instrument 10 is suitably designed to provide a means for connecting a piece of tubing 26 to the sampling instrument 10. The diameter of the proximal end 24 may vary but must be sufficient to provide for the passage of collected cells through the sampling instrument 10.

The sampling instrument 10 of the present invention is preferably made of a material capable of withstanding sterilization procedures commonly used by those skilled in the art. Thus, the sampling instrument 10 of the present invention is preferably made of a material capable of withstanding temperatures of at least about 150° C. and capable of withstanding exposure to chemicals such as solvents, gases, and acids used in conventional sterilization procedures. Preferred materials of the present invention include, but are not limited to, plastic, glass, ceramic, and metal.

The method and device of the present invention provides a means for suctioning 30 dislodged cytological material under negative pressure through the sampling instrument 10 and substantially immediately into fixative 34 contained in a fixative container 32. As used herein, negative pressure refers to gas pressures below the normal atmospheric pressure of about 760 torr or 1 millimeter of mercury. Preferably, a negative pressure of from about 20 millimeters of mercury (mmHG) to about 75 mmHG is applied to the sampling instrument. The suctioning means 30 comprises a source of negative pressure 30 and may include any standard suctioning means known to those skilled in the art. Suctioning means 30 can therefore include, mechanical rotary oil-sealed vacuum pumps, vapor pumps, and self-contained vacuum-containers (referred to a Vacutainer™). With respect to the latter, such Vacutainer™ are releasably sealed vacuum containers are used which, upon the release of such vacuum, are able to suction up cytological material (represented in FIG. 4).

Prior investigators have used sampling devices having suction bulbs or syringes to collect cells. Such devices, however, are incapable of creating the degree or consistency of suction as does the suctioning means of the present invention. Furthermore, conventional devices do not protect the healthcare worker from direct exposure to the potentially contaminated cytological material. For example, the suction afforded by devices described by Hasselbrack, U.S. Pat. No. 4,620,548 and Ayre, U.S. Pat. No. 3,540,432 is limited to the suctioning capacity of the bulb utilized and suffer because the bulb should properly only be squeezed once during the sampling process to prevent excessive exposure of collected cells to air. Repeated aspirations of cytological material by successive squeezing of a bulb causes undesired exposure to air and hence, increases the likelihood of collected cells undergoing morphological changes. Such repeated aspirations also increase the risk that desired cytological material will be irretrievable due to the material being suctioned into the bulb itself. In addition, due to the anatomic size and orientation of the uterine cervix and the design and operation of conventional devices, the healthcare worker typically requires the use of both hands to hold and move the sampling device along the desired site and to operate the manual suction bulb.

According to one embodiment of the present invention, the healthcare worker dislodges cytological samples by scraping the leading edge of the distal end 12 of the sampling instrument 10 across the surface of tissue at the site of collection. Simultaneously, continuous negative pressure is applied to the sampling instrument 10 by a suctioning means 30 capable of drawing cytological material substantially immediately into the opening of the tubular channel 28 of the sampling instrument 10. The healthcare worker can therefore use the present invention to collect a pre-determined or desired amount of cytological material. The present invention allows good comparative data to be obtained from sample to sample due to the ability of the present method to reproducably collect substantially similar amounts of material, sc amount visually verified during the sampling operation. In addition, the application of continuous negative pressure ensures that the collected cytological material that is fixed and assayed includes only material that has been drawn directly into the sampling instrument 10. This is in contrast to cytological samples collected by previously described collection devices that included cells that stuck to the outside of the portion of the collection instrument until being transferred to fixative (i.e., see U.S. Pat. No. 3,540,432 by Ayre; U.S. Pat. No. 4,620,548 by Hasselbrack; and U.S. Pat. No. 4,633,886 by Bucaro). Because the present invention precludes the collection and analysis of undesired cells that may have suffered morphological changes by being exposed to air, the present invention reduces the instances of cell morphology misinterpretation by cytologists.

In one embodiment, the sampling instrument 10 of the present invention can be interconnected with a source of negative pressure 30 through tubing 26. Any tubing can be used that has sufficient flexibility to allow for movement of the tubing 26 during sampling operations and which has a sufficient diameter through which the desired amount of tissue may be collected.

According to the method of the present invention, collected cytological material is fixed substantially immediately before such material is exposed to a quantity of air sufficient to substantially affect the morphology of such material. Fixation is achieved in a manner so that the material can be histocyologically stained to facilitate subsequent analysis. As used herein, substantially immediate fixation refers to the fixation of such material prior to the material undergoing substantial morphological changes that would jeopardize the correct analysis of such material and more particularly refers to the fixation of such material within preferably about 0.5 seconds from the time of dislodgement, less preferably up to about 2 seconds but not more than 5 seconds depending upon various factors affecting the drying of cells and fixation. Substantially immediate fixation is required to maintain the morphology of the collected cells so that they appear substantially identical to the way the cells present themselves in the living tissue prior to collection.

As used herein, fixation refers to the subjection of cell to a chemical capable of killing the cell, permeabilizing the cellular membrane, and chemically cross-linking cellular components, thus making the cellular proteins insoluble. Loss of cellular fluid and cross-linking of cellular components essentially stabilizes and "locks" cellular components in position, thereby preventing morphological change by removing cellular fluid and replacing it with fixative. Permeabilization of the cellular membrane also enables reagents used to detect cellular morphology, such as stains and antibodies, to enter the cell. Treatment of cells with fixative also prevents deterioration of the cells due to autolysis and degradation by bacteria and mold and fungus. Fixatives often include acids or organic solvents such as alcohols, and reactive aldehydes, particularly glutaraldehyde and formaldehyde.

Previously described collection devices disclose exposing collected cells to glycerin (i.e., see U.S. Pat. No. 4,633,886 to Bucaro Jr. and U.S. Pat. No. 3,540,432 to Ayre). Exposure of cells to glycerin, however, does not immediately kill the cells, nor is glycerin treatment capable of removing cellular fluid from the cells and cross-linking cellular components. Additionally, the isotonic action of glycerin can not render infectious agents non-infectious, thus exposing healthcare workers to risk of infection from unknown pathogens. Glycerin is typically used by those skilled in the art to maintain the isotonic integrity of the cells and, at certain concentrations, to swell cells.

During the fixation step of the present invention, disengaged cytological material is drawn through the sampling instrument 10 under negative pressure into a means for fixing the cytological material 32. The fixing means 32 contains a sufficient amount of fixative 34 to fix the volume of cytological material collected. Cytological material is contacted with fixative 34 in any manner effective to fix such material and can entail the complete or partial immersion of such material in fixative. In one embodiment of the present invention, dislodged cells are suctioned directly into a pre-determined amount of fixative by means of a constant vacuum source.

Suitable fixatives of the present invention include any fixative capable of maintaining the morphology of collected cytological material by removing cellular fluid from collected cells. Such fixatives may be in the form of a liquid, gel, foam, or powder and may include, but are not limited to, ethanol, acetone, methanol, osmiumtetroxide, mercuric chloride, formaldehyde, polypropylene glycol, polyethylene glycol, EDTA, or any combination thereof. A preferred liquid fixative of the present invention is ethanol and a preferred powder fixative is formaldehyde.

The fixing means 32 of the present invention comprises any means capable of holding a sufficient amount of fixative and that is capable of being operatively connected to a suctioning means 30 and a dislodging means 10. The fixing means 32 can be of any desired shape, including tubular, cylindrical, flat, etc., and may comprise, for example, boxes, test tubes, petri plates, flasks, beakers, hollow slides, graduated cylinders, bags or bottles.

In one embodiment, the fixing means 32 of the present invention is a fixative container 32 having one or more openings 38, 40 sufficient to allow passage of collected cytological material into the container and to allow application of a source of negative pressure 30. The fixative container 32 may be suitably designed such that variable volumes of fixative 34 may be stored in the container 32, depending upon the amount of cytological material the healthcare worker needs to collect. The volume of fixative 34 contained in the fixative container 32 should be a sufficient amount to substantially contact all collected cytological material with fixative 34.

In one embodiment of the present invention, referring to FIG. 1, the fixative container 32 comprises a container having a lid 36 which has an inlet valve 38 and an outlet valve 40. The inlet valve 38 has a means for attaching tubing 26 which allows for passage of cytological material into the fixative container 32. The outlet valve 40 has a means for attaching tubing 26 and operatively connects the fixative container to a source of negative pressure 30. The lid 36 is designed such that the inner environment of the fixative container 32 is effectively sealed from exposure to the environment outside of the container 32.

Figure 2:
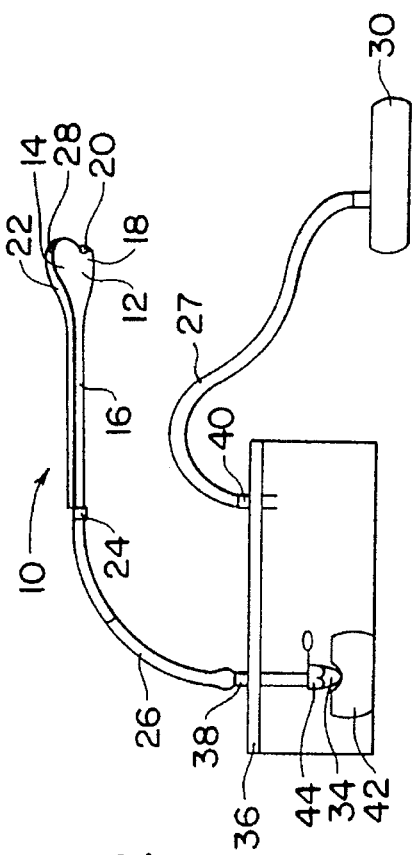
FIG. 2 is a schematic diagram of another embodiment of the cytological sampling device of the present invention.

In another embodiment of the present invention, referring to FIG. 2, a fixative container 32 comprises a container of sufficient size to accommodate one or more racks 42 for holding one or more test tubes 44 containing fixative. Preferred test tubes appropriate for collection of cytological material include test tubes with conical-shaped or rounded bottoms. The fixative container 32 is suitably designed such that a test tube 44 can be positioned directly below the inlet valve 38 through which collected cytological material is directed during sampling operations.

Figure 3:
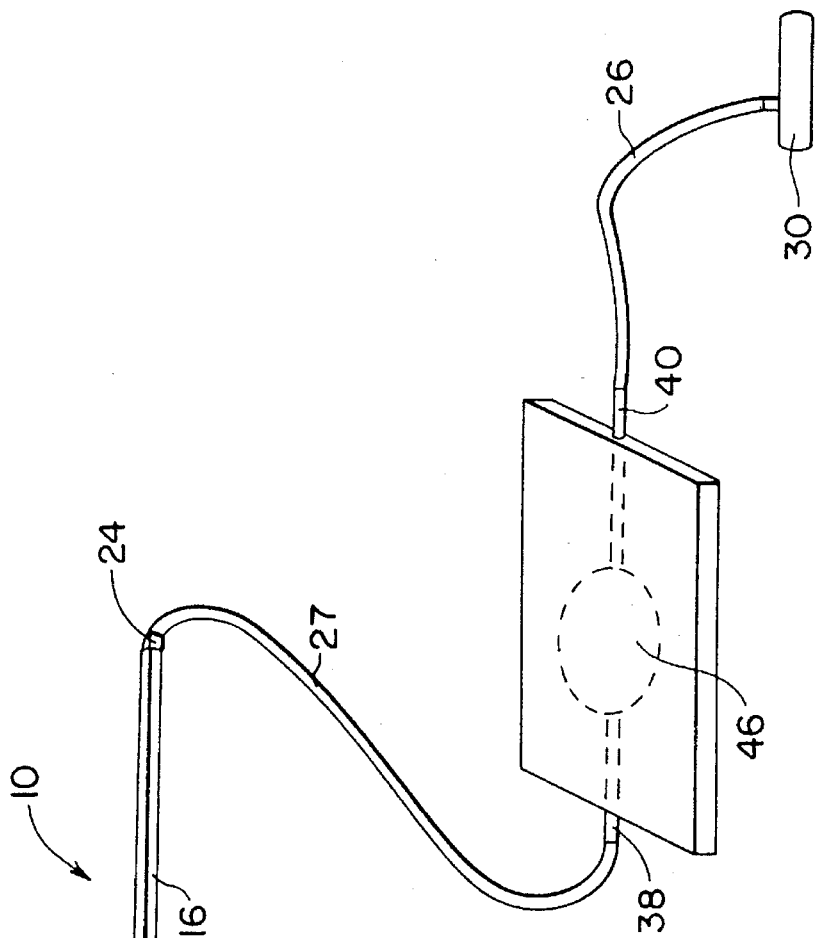
FIG. 3 is a schematic diagram of one embodiment of the cytological sampling device of the present invention used for direct viewing under a microscope.

In yet another embodiment of the present invention, referring to FIG. 3, a fixative container 32 comprises a container having suitable dimensions to fit on the stage of a microscope. The container 32 has an essentially flat rectangular shape and has a chamber 46 capable of holding fixative. Projecting from opposite ends of the chamber is an inlet 38 to allow entrance of cytological material into the chamber and an outet 40 to which a source of negative pressure may be applied. The container 32 and the chamber 46 are composed of material suitable for direct visualization of cytological material under a microscope, such material preferably being glass or clear plastic.

Figure 4:
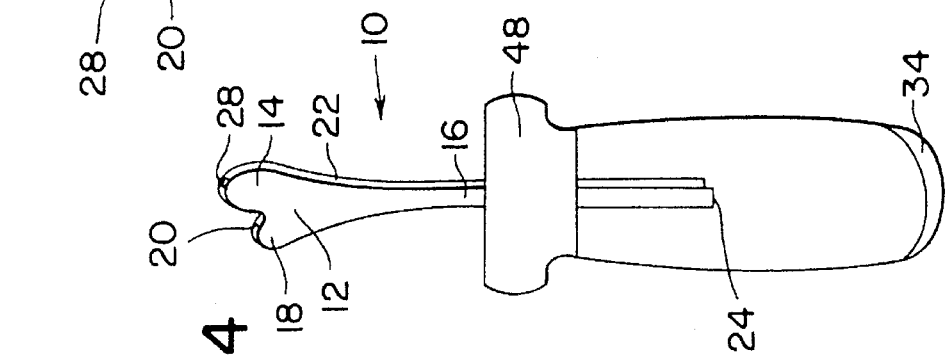
FIG. 4 is a schematic diagram of an alternative embodiment of the cytological sampling device of the present invention.

In an alternative embodiment of the present invention, referring to FIG. 4, the fixative container 32 comprises a test tube-shaped container 32 having an open end fitted with a seal 48 that conforms to the interior diameter of the container 32. The seal 48 has an inlet 38 through which a sampling instrument 10 can be inserted. The fixative 34 is sealed under negative pressure so that essentially all air is evacuated from the container 32. Cytological material can be drawn into the sampling instrument 10 upon the release of such negative pressure. Cytological samples collected using the test tube container 32 may allow for convenient shipment of cytological samples through the mail. Further, the use of dry fixative powders may alleviate complications of seepage of liquid fixatives through mailing packages should the fixative container break during shipment.

The fixative container 32 of the present invention is preferably constructed of a clear material through which collection of cytological material can be visually monitored. The container 32 should also be composed of a material resistant to chemicals found in fixatives, preferred materials being glass and chemical resistant plastics. The lid 36 should be composed of material capable of creating a seal when negative pressure is applied to the fixative container 32, preferably rubber or flexible plastic.

In one embodiment of the method of the present invention, prior to collection of cytological material, a suitable amount of fixative 34 is placed in the fixative container 32. One end of a piece of tubing 26 is attached to the inlet valve 38 of the lid 36 and the other end is attached to a sampling instrument 10. A second piece of tubing 27 is attached to the outlet valve 40 of the lid 36 and the other end is attached to the source of negative pressure 30. Negative pressure is applied to the fixative container 32 by operation of the source of negative pressure 30. As such, an essentially negative pressure system is established between the sampling instrument 10 and the fixative container 32. Using the sampling instrument 10, a healthcare worker collects a cytological sample from a tissue source. Contact between the sampling instrument 10 and the tissue is maintained until a sufficient amount of cytological material has been collected. As used herein, a sufficient amount of cytological material refers to the amount of cytological material needed to analyze the morphology of a representative population of cytological material from a particular tissue for a desired purpose. Preferably, cytological material collected for PAP smears comprise from about 100,000 to about 250,000 cells per cubic centimeter. The collected cytological material is drawn through the sampling instrument 10 and substantially immediately into fixative 34 so that the cytological material is not substantially exposed to the atmosphere outside of the fixative container 32. The collected cytological material may be further contacted with the fixative 34 by agitating the fixative container 32. The fixed cytological material may then be deposited directly, with or without further concentration, in or on the means by which the samples are to be assayed. For example, fixed cytological material can be assayed on slides, coverslips, enzyme-linked immunoassay plates, and other substrates suitable for analysis of the cytological material. As discussed above, some embodiments of the present invention permit direct microscopic analysis of dislodged cells without the need to remove such cells from the collection container (see FIG. 3).

In another embodiment of the method of the present invention, referring to FIG. 4, a test tube-shaped container 2 (herein referred to as a vacutainer) with fixative 34 stored under negative pressure can be used to collect cytological samples. A healthcare worker contacts a tissue sample site with the sampling instrument 10 and negative pressure is released by inserting the proximal end 24 of the sampling instrument 10 through the seal 48 of the container 32. The released negative pressure draws cytological material through the sampling instrument 10 into the fixative 34 contained in the container 32. The collected cytological material may be further contacted with the fixative 34 by agitating the fixative container 32. The fixed cytological material can then be assayed by a variety methods including those discussed below.

Following the preparation of fixed cytological material for morphological analysis, fixed cytological material may then be screened for products, components, and to determine whole cell morphology using known assays. Certain stains bind preferentially to different cellular components. For example, certain organic dyes bind preferentially to negatively charged molecules such as DNA and RNA or to nuclear or plasma membranes. Additionally, certain cellular enzymes may be exposed to molecular substrates to produce a localized visible product upon reaction with the enzyme. Antibodies coupled to enzymes, fluorescent dyes or radioactivity may also be used to determine the distribution of cellular components within a fixed cell. For morphological analysis, fixed cytological material can be deposited on glass slides by monolayering and allowed to adhere to the slide. Prior to being analyzed for morphological changes, the cells are stained with histological stains including, for example, modified papanicolaou stain, modified haematoxylon eosin-azure stain, orange G, and fluorescent stains such as acridine and Hoerscht. Alternative histochemical staining can be performed to locate and identify, for example, intracellular enzymes to specific subcellular compartments. Fixed cells may also be assayed using antibodies conjugated to radioactive, fluorescent, or enzyme labels to detect intracellular and extracellular cellular compounds.

Morphological analysis of histochemically stained cytological material may be performed by cytotechnologists or by automated screening devices. A variety of automated systems have been developed for analysis of cytological samples. Such automated systems include, but are not limited to, "Autocyte" (Roche Imaging Analysis Systems, Elon College, N.C.), "AutoPap™ 300 Automatic Pap Screener"

(NeoPath, Bellevue, Wash.), "Amcell 2000T Labmaster™" (Accuron Corp., Cleveland, Ohio), "Papnet™" (Neuromedical Systems, Inc., Sufforn, N.Y.), and "The Cytyc System for Cervical Cytology™" (Cytyc Corp., Marlborough, Mass.). The method and device of the present invention is well suited for use with these automated systems and afford unprecedented consistency and accuracy of results. Combining the method and device of the present invention with automated systems reduces the problem of inaccurate sampling and therefore causes a decrease in false negative results.

Importantly, the method and device of the present invention also reduces direct contact between the healthcare worker and the tissue or fluids potentially infected with HIV or other infectious agents. The sampling instrument of the present invention enables the healthcare worker to sample potentially infected tissue without directly contacting the tissue. Moreover, because collected cytological material collected in accordance with the present method and device is fixed substantially immediately following dislodgement of the material, the healthcare worker only handles fixed material when, for example, the material is transferred to a microscope slide. While not being bound by theory, it is believed that the fixation process is capable of chemically cross-linking viral protins to each other as well as to other cellular proteins. As such, potentially infectious viral particles are made essentially non-infectious by chemical cross-linking. Moreover, as discussed above, some embodiments of the present invention totally isolate the healthcare worker from collected material to be analyzed because the collection, fixation and analysis can be performed without removing or transferring the collected material from the fixative container (see FIG. 3). The present method and device therefore provide means for complying with recent OSHA regulations relating to the handling of potentially infectious materials.

The following examples are provided for the purposes of illustration and are not intended to limit the scope of the invention.

EXAMPLES

Example 1

Collection of Cytological Samples using a Negative Pressure Sampling System.

A cytological sample is collected by contacting a spatula sampling instrument to a tissue site and drawing cells into a container containing fixative under negative pressure.

Approximately 10 to 25 milliliters (ml) of fresh fixative comprising 20% ethanol and 2% polypropylene glycol is placed inside a fixative container. The lid is secured onto the container. The tubing leading from the outlet valve of the fixative container s connected to a mechanical vacuum system. A sterile spatula sampling instrument is placed at the end of the tubing leading from the inlet valve of the fixative container. Approximately 30 mmHG of vacuum is applied to the system. The sterile spatula is then contacted to the face of the cervix uteri and/or the endocervical canal and is passed over the tissue in a scraping motion. At least about 100,000 cells per cubic centimeter are collected. The cells are allowed to remain in the fixative until transported to the cytology laboratory and the healthcare worker is able to transfer the fixed cells to a glass slide for processing for morphological analysis.

Following transfer of the fixed cells to a glass slide, the cells are allowed to adhere to the slide by drying and then stained using a modified papanicolaou stain method. The cells are then viewed under a microscope for morphological analysis.

Example 2

Collection of Cytological Samples using a Vacutainer System.

A cytological sample is collected by contacting a spatula sampling instrument to a tissue site and applying negative pressure using a vacutainer.

The vacutainer is coated with approximately 1.5 to 3.0 milligrams of a powdered fixative. A sterile spatula sampling instrument is contacted to the face of the cervix uteri and/or the endocervical canal. Simultaneously, the sterile sampling instrument is inserted into the seal of the vacutainer and passed over the tissue in a scraping motion. At least about 100,000 cells per cubic centimeter are collected. The tube is then mildly agitated to ensure fixation of all the collected cells. The cells may remain in the fixative until the healthcare worker is able to transfer the fixed cells onto a glass slide for morphological analysis.

Following transfer of the fixed cells to a glass slide, the cells are allowed to dry to the slide and then stained using a modified papanicolaou stain method. The cells were then viewed under a microscope for morphological analysis.

Example 3

Collection of Cytological Samples into a Sampling Slide.

A cytological sample is collected by contacting a spatula sampling instrument to a tissue site and drawing cells under negative pressure into a container containing fixative, the container being designed for direct viewing of the collected cells under the microscope.

Approximately 0.05 microliters of fresh fixative comprising 30% ethanol and 2% polypropylene is placed inside a the chamber of the collection slide. Tubing leading from the outlet valve of the collection slide is connected to mechanical vacuum system. A sterile spatula sampling instrument is placed at the end of tubing leading from the inlet valve of the fixative container. Approximately 20 to 30 mmHG of vacuum is plied to the system. The sterile spatula is then contacted to the face of the cervix uteri and/or the endocervical canal and passed over the tissue in a scraping motion until about 100,000 cells are collected. Negative pressure is continuously applied until substantially all of the fixative has evaporated from the chamber, leaving the collected cells behind. A modified haematoxylon eosinazure orange G cocktail is then added to the chamber containing the fixed cells and allowed to sit for about 1.5 minutes prior to addition of rinsing solutions comprising 95% alcohol and absolute alcohol. The cells are then viewed under a microscope. As such, the healthcare worker need not handle the cells directly for morphological analysis.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A method for analyzing cytological material, comprising:

a) collecting cytological material from tissue selected from the group consisting of the ectocervix, the squamocolumnar junction, and the endocervix, wherein said collecting step includes fixing said cytological material substantially immediately by suctioning said cytological material directly into a container containing a sufficient amount of a fixative to fix said collected cytological material; and b) analyzing said cytological material.

2. The method of claim 1, further comprising analyzing said collected cytologic material for the physical location, origin and identification of intracellular and extracellular morphologic characteristics.

3. The method of claim 1, wherein said step of analyzing is performed using a technique selected from the group consisting of standard, semiautomated and automated cytologic specimen screening techniques.

4. The method of claim 1, wherein said collected cytological material is contacted with fixative prior to said cytological material undergoing significant morphological changes due to exposure to air.

5. The method of claim 1, wherein said step of collecting is performed within about 0.5 seconds to about 5 seconds after said suctioning of said cytological material.

6. The method of claim 1, wherein said cytological material is collected under negative pressure from about 20 mmHG to about 75 mmHG.

7. The method of claim 1, wherein said collecting step comprises collecting a pre-determined amount of cytological material.

8. A method for analyzing Papanicolaou cytological specimens, comprising:

a) collecting cytological material from the squamocolumnar junction of a cervix uteri, said step of collecting comprising scraping the squamocolumnar junction using a sampling instrument suitably designed to contact mucous membrane tissue, said instrument operatively attached to a means for suctioning and suctioning said cytological material into a container containing a sufficient amount of fixative to fix said cytological material, said cytological material contacting said fixative within about 0.5 seconds to about 5 seconds of said collection of said cytological material; and b) analyzing said cytological material using a technique selected from the group consisting of standard, semiautomated and automated cytologic specimen screening techniques.

9. A method for analyzing cytological material, comprising:

a) suctioning cytologic material directly into a container having fixative contained therein such that said collected cytologic material is substantially immediately fixed; and b) analyzing said cytologic material.

10. The method of claim 9, wherein said step of collecting comprises using a sampling instrument operatively attached a source of negative pressure.

11. The method of claim 10, wherein said negative pressure is continually applied during said step of suctioning.

12. The method of claim 10, wherein said negative pressure allows the collection of a predetermined amount of cytological material.

13. The method of claim 9, wherein said material is not exposed to the atmosphere outside said fixative container prior to being fixed.

14. The method of claim 9, wherein said fixative is selected from the group consisting of ethanol, acetone, methanol, osmium tetroxide, mercuric chloride, formaldehyde, acetic acid, polypropylene glycol, polyethylene glycol, EDTA, and any combination thereof.

15. The method of claim 9, wherein said cytological material is sampled from the cervix uteri.

16. The method of claim 9, wherein said collecting step does not involve any direct bodily contact with said collected cytological material by a health care worker following dislodgement of said cytological material.

* * * * *